United States Patent [19]

Calcaterra et al.

[11] Patent Number: 4,717,544
[45] Date of Patent: Jan. 5, 1988

[54] METHOD OF STERILIZATION USING A SUSTAINED RELEASE DISINFECTANT

[75] Inventors: Lidia T. Calcaterra, Arlington Heights; Harry W. Gibson, Lake Zurich, both of Ill.

[73] Assignee: Allied-Signal Inc., Morristown, N.J.

[21] Appl. No.: 889,155

[22] Filed: Jul. 25, 1986

[51] Int. Cl.[4] .................. A01N 35/04; A61L 2/20; A61L 9/02
[52] U.S. Cl. ........................ 422/36; 422/28; 422/29; 514/693; 514/705
[58] Field of Search ............... 422/36, 28–29; 514/693, 705

[56] References Cited

U.S. PATENT DOCUMENTS

| | | | |
|---|---|---|---|
| 2,831,749 | 4/1958 | Marinaro et al. | 422/36 X |
| 3,310,364 | 3/1967 | Rijssenbeek | 422/36 |
| 3,983,252 | 9/1976 | Buchalter | 422/36 X |
| 4,050,576 | 9/1977 | Williams et al. | 422/36 X |
| 4,128,397 | 12/1978 | Lynch | 422/29 |

OTHER PUBLICATIONS

Lucas & Mendes, *J. Hyg., Camb.*, 84, 41, (1980).
Bovallius & Anas, *Applied & Environmental Microbiology*, 34, 129, (1977).

*Primary Examiner*—Barry S. Richman
*Assistant Examiner*—Lynn M. Kummert
*Attorney, Agent, or Firm*—Thomas K. McBride; John F. Spears, Jr.; Eugene I. Synder

[57] ABSTRACT

Materials in a closed or semi-closed environment can be effectively disinfected by thermally depolymerizing solid polymeric aldehydes which are in equilibrium with gaseous monomer acting as the disinfecting agent. Glutaraldehyde is a particularly effective disinfectant, and polyglutaraldehyde maintains its effectiveness by releasing the gaseous monomer at a slow, controlled rate over many days.

6 Claims, No Drawings

METHOD OF STERILIZATION USING A SUSTAINED RELEASE DISINFECTANT

BACKGROUND OF THE INVENTION

The disposal of infectious wastes, especially in a hospital environment, is a perennial problem. What is needed is an inexpensive, effective method of killing a myriad of infectious organisms over the period of use of a disposable container. What is available is an assortment of approaches which incompletely and imperfectly addresses this need. What is taught and offered in this application is a better solution to the needs of the marketplace.

One approach, already commercialized, uses a buffered solution of sodium pyrosulfite (sodium metabisulfite, $Na_2S_2O_5$) to release sulfur dioxide as a vapor phase bactericide at a controlled rate so as to maintain its concentration in the container at 75-150 ppm over a period of several weeks, the concentration being sufficient to kill all bacteria in about 24 hours. C. M. Lucas and M. F. Mendes, *J. Hyg. Camb.*, 84, 41 (1980); cf. U.S. Pat. No. 4,128,397. The use of a gas has the advantages of completely filling the container with a bactericide so that all surfaces are in contact with the disinfectant. Because of the high permeability of gases through many materials containing infectious microorganisms, disinfecting gases also may contact interior surfaces inaccessible to liquids, thereby acting more efficaciously.

Many gas phase disinfectants are known, including sulfur dioxide, glyoxal, iodine, chlorine, malondialdehyde, glutaraldehyde, methylene chloride, formaldehyde, and ammonia. It is not necessary that a gas phase disinfectant be a vapor at normal temperatures, but only that the material has a sufficiently high vapor pressure that its gas phase concentration at its intended temperature of use be sufficiently high to impart bactericidal properties. Recently Bovallius and Anas, *Applied and Environmental Microbiology*, 34, 129 (1977) have reported that glutaraldehyde is an effective gas phase surface disinfectant at a concentration between 15-20 mg/m$^3$ for a broad variety of infectious microorganisms and bacterial spores. This latter observation is especially significant since spores generally are inherently difficult to kill.

The objective sought was a slow release, gas phase disinfectant. The evaluation of various available gas phase disinfectants pointed to aldehydes such as glutaraldehyde as being particularly effective and therefore are specially desirable disinfectants. The problem then became how to obtain a slow, controlled, and sustained release of gas phase aldehydes. Since aldehydes are susceptible to oxidative degradation a related problem was how to maintain the stability of an aldehyde during storage. Another but by no means unimportant consideration was to achieve such results at low cost, in a manner conducive to its use in a variety of operating environments, and to achieve such results efficiently.

SUMMARY OF THE INVENTION

The purpose of this invention is to provide a system which slowly releases a gas phase disinfectant and which shows storage stability, ease of handling, and effectiveness against a broad spectrum of pathogens. An embodiment comprises thermally depolymerizing solid polymeric aldehydes to afford gas phase monomers which are disinfectants. In a more specific embodiment the solid is polyglutaraldehyde. In a still more specific embodiment the polyglutaraldehyde is depolymerized at a temperature from about 10° to about 80° C.

DESCRIPTION OF THE INVENTION

The object of this invention quite simply was to obtain the slow, controlled release of a gas phase disinfectant in the presence of the material to be disinfected. The identification of aldehydes as the most desirable class of disinfectants, and of a gluteraldehyde as the preferred aldehyde, more specifically defines the object. But as is usual stating the object is simple, but constructing the solution is difficult. In the present case the solution must satisfy several constraints. The system must be operable over the broad temperature range from about 10° to about 80° C. The disinfectant should be released sufficiently rapidly that the kill concentration is achieved within about 1-2 hours, yet gradually enough so as to sustain the kill concentration over several days. The slow release system must be physically and chemically stable, easily handled by untrained personnel, non-toxic to people in the environment in which it is used, and compatible with the materials of construction of the disposable containers.

These criteria are generally met by solid polymeric aldehydes which undergo thermal depolymerization to afford aldehydes which are gaseous, or have a substantial vapor pressure, between 10° and 80° C. Such polymeric aldehydes include polymers of glyoxal, formaldehyde, malondialdehyde, and glutaraldehyde, with the latter being especially desirable. In particular, polymers such as polyglutaraldehyde are known to be in equilibrium with monomeric aldehyde in the gas phase according to the equation,

where M(g) is monomer in the gas phase and (s) designates the solid phase. The solid polymers are stable, in contrast to the monomeric aldehydes which readily undergo autoxidation. Thus, the solid polymeric aldehydes can be stored over long periods without adverse effects in practicing this invention.

The disinfecting action in the present invention is particularly directed to a nominally closed system, such as a plastic bag in a container for infectious wastes. Therefore one needs at temperatures between about 10° and about 80° C. a monomer aldehyde whose vapor pressure is sufficiently high as to afford a kill concentration of gas phase aldehyde. That is, the concentration of the gaseous aldehyde needs to be sufficiently high to kill the infectious organisms within a reasonable time. Stated differently, the vapor pressure of the monomeric aldehyde in equilibrium with its solid polymer needs to be high enough to afford a concentration lethal toward those organisms against which it is effective, and equilibrium needs to be established within a few hours. Polyglutaraldehyde is especially effective because it affords gaseous glutaraldehyde at a concentration between about 10 and about 20 mg/m$^3$ at equilibrium over the aforementioned temperature range. Although our invention is readily practiced within the temperature range between about 10° and about 80° C., it is preferable to practice this invention between about 15° and about 40° C.

There are additional advantages to the use of polyglutaraldehyde as the source of a gas phase disinfectant. The release of gaseous polyglutaraldehyde is relatively constant over 10–15 days at about ambient temperature, with 3–4% being released per day. Therefore there is a sustained release of gaseous glutaraldehyde from solid polyglutaraldehyde. The amount released is also approximately proportional to the surface area of the solid polyglutaraldehyde. Therefore there is afforded a simple method of controlling the amount of gas phase glutaraldehyde released, at least in principle; the greater the surface area of the solid polyglutaraldehyde, the greater will be the amount of gaseous glutaraldehyde released, at least until the equilibrium concentration is reached. Another advantage of solid polyglutaraldehyde is that equilibrium with the gas phase monomeric glutaraldehyde is rapidly established. This means that in a closed or semi-closed system the kill concentration can be reached within 1–2 hours. Yet another advantage of solid polyglutaraldehyde is that it may be completely utilized in affording gaseous glutaraldehyde, thereby being an efficient source of gaseous glutaraldehyde and leaving no residue.

Any solid polymeric aldehyde which may be thermally depolymerized to afford a gaseous monomeric aldehyde may be used in the practice of this invention. The method of preparation of such solid polymeric aldehydes is unimportant. For example, in the case of polyglutaraldehyde preparation may be via the technique of crystallization polymerization, as described within, or it may be a base-catalyzed low temperature polymerization. The degree of polymerization also will vary but generally the solid polymer need not contain more than about 20 monomeric residues, at least on the average, although higher degrees of polymerization may not be disadvantageous.

The invention may be simply practiced in a number of discrete ways. Using polyglutaraldehyde as an example, the solid can be shaped as pellets placed in a perforated container attached to the walls of a garbage bag. While stored there will be little loss through thermal depolymerization because the closed garbage bag can be thought of as a sealed container with a very small volume, such that the equilibrium vapor pressure is quickly reached with no measurable loss of polyglutaraldehyde. Upon opening the bag and placing it in a hamper thermal depolymerization to afford gaseous glutaraldehyde begins at once with the entire system acting as a semi-closed container. Thermal depolymerization readily and rapidly affords gaseous glutaraldehyde with equilibrium being quickly reached after the container is closed. While the container is closed little glutaraldehyde escapes and there is little loss of polymeric glutaraldehyde. Some vapor is lost whenever the container is opened, but the equilibrium gas phase concentration is quickly reestablished.

Another way of practicing this invention is to shape the polyglutaraldehyde as a solid block whose surface area will increase as the volume of the closed container increases. Over the surface may be placed a piece of plastic or thick paper in adhesive contact with the surface so as to prevent thermal depolymerization during transit. When the garbage bag is opened, the plastic or paper covering the solid block of polyglutaraldehyde may be removed with release of gaseous glutaraldehyde beginning immediately by thermal depolymerization. Yet another means of practicing this invention is to coat, for example, the plastic surface of a garbage bag with polyglutaraldehyde itself.

The following examples are only illustrative of this invention which is not to be limited thereto.

EXAMPLE 1

Preparation of Polyglutaraldehyde

Approximately 40 mL of a 70% w/v aqueous glutaraldehyde solution was measured into an oven dried flask. Anhydrous ethyl ether, 200 mL, was added to the glutaraldehyde solution. The water layer was removed by pipetting and anhydrous sodium sulfate was added to the mixture to absorb traces of water. The solution was then carefully filtered into an oven dried round bottom flask and the ethyl ether was removed by evaporation. The remaining glutaraldehyde was then distilled using a Kugelrohr under a vacuum of 8–10 mm Hg at an air bath temperature of 75° C. to 80° C. The neat glutaraldehyde was poured into an oven dried sample vial, stoppered with a rubber septum, and blanketed with a nitrogen atmosphere. The product was frozen at $-70°$ C. until analyses by differential scanning calorimetry and infrared spectroscopy were performed. A small portion of the liquid product was allowed to polymerize in an open vial at room temperature. Infrared analysis of the resulting solid gave a number-average degree of polymerization for the polymer of 3–5.

EXAMPLE 2

Antimicrobial efficacy of gaseous glutaraldehyde from thermal depolymerization of polyglutaraldehyde The vapors from 150 mg of polyglutaraldehyde at 20° C. were allowed to saturate the atmosphere of a sealed 25 L chamber for a period of 24 hrs. All operations were carried out using aseptic techniques. The humidity in the chamber was maintained at 8%.

A portion of *Staphylococcus aureus* ATCC 27217 from a freshly grown slant was added to 50 mL of bacto agar broth and allowed to grow to 0.10 OD ($10^7$ bacteria/mL). A portion of this broth was further diluted in 2.5% letheen broth to ca $10^6$ bacteria/mL (dilution "A"). A 20 uL sample was pipetted from dilution "A" in triplicate at 3 minute intervals into sterile glass boats. The boats containing the bacteria were placed in the chamber containing the polyglutaraldehyde vapor-saturated atmosphere for 1 hour. A control also was run in triplicate following the same procedure except that the bacteria were not exposed to the polyglutaraldehyde-generated atmosphere. A portion of dilution "A" was also further diluted and plated for the quantitative analysis of bacteria present before the 1 hour exposure.

After 1 hour the boats containing bacteria were then flushed with 1 mL of sterile 0.9% saline solution into sterile vials (1/50 dilution labeled dilution "B"). A portion of dilution "B" was further diluted 1/50 to give dilution "C", and a portion of dilution "C" was diluted to 1/50 to give dilution "D". 100 uL from dilutions B, C, and D were pipetted and plated on bacto agar plates. The plates were incubated overnight, the colonies were counted, and the growth or kill of bacteria was observed. Results are shown in Tables I and 2.

TABLE I

| EFFICACY OF VAPORS FROM POLYGLUTARALDEHYDE AGAINST *S. AUREUS* | | | |
|---|---|---|---|
| | CFU[a] | Average[b] | % Reduction |
| ACTUAL | | | |
| A | 412 | $9.53 \times 10^6$ | |
| B | 344 | | |
| B | 346 | | |
| B | 420 | | |
| CONTROL - DILUTION B | | | |

TABLE I-continued
EFFICACY OF VAPORS FROM POLYGLUTARALDEHYDE AGAINST S. AUREUS

| | CFU[a] | Average[b] | % Reduction |
|---|---|---|---|
| 1 | 487 | $1.32 \times 10^7$ | |
| 2 | 542 | | |
| 3 | 550 | | |
| CONTROL - DILUTION C | | | |
| 1 | 10 | $1.63 \times 10^7$ | |
| 2 | 10 | | |
| 3 | 18 | | |
| SAMPLE - DILUTION B | | | |
| 1 | 0 | $<<2.5 \times 10^4$ | |
| 2 | 0 | | |
| 3 | 0 | | >99.9 |
| SAMPLE - DILUTION C | | | |
| 1 | 0 | $<<2.5 \times 10^4$ | |
| 2 | 0 | | |
| 3 | 0 | | |

[a] Colony Forming Units.
[b] Number of bacteria per mL of solution.

TABLE 2
EFFICACY OF VAPORS FROM POLYGLUTARALDEHYDE AGAINST S. AUREUS

| | CFU[a] | Average[b] | % Reduction |
|---|---|---|---|
| ACTUAL | | | |
| A | 349 | $8.78 \times 10^6$ | |
| A | 311 | | |
| B | 396 | | |
| B | 346 | | |
| CONTROL - DILUTION B | | | |
| 1 | 429 | $1.13 \times 10^7$ | |
| 2 | 505 | | |
| 3 | 416 | | |
| CONTROL - DILUTION C | | | |
| 1 | 48 | $8.5 \times 10^6$ | |
| 2 | 33 | | |
| 3 | 20 | | |
| SAMPLE - DILUTION A | | | |
| 1 | 1 | $1.1 \times 10^4$ | |
| 2 | 2 | | |
| 3 | 62 | | 99.6 |
| SAMPLE - DILUTION B | | | |
| 1 | 0 | $7.5 \times 10^4$ | |
| 2 | 0 | | |
| 3 | 10 | | |

[a] Colony Forming Units.
[b] Number of bacteria per mL of solution.

EXAMPLE 3

Determination of gaseous glutaraldehyde released from polyglutaraldehyde

About 5 gms of polyglutaraldehyde was ground to a medium fine mesh. Five petri dishes were preweighed and a sample of polyglutaraldehyde placed in each of the 5 dishes. The dishes were then reweighed; weights ranging from 700 mg to 900 mg per dish. The samples were allowed to remain open to the atmosphere at ambient temperature for 21 days and were weighed on a daily basis at 24 hr. intervals except for weekends. The daily weight was noted as loss in grams and percent weight lost over a period of 21 days. The composite results are shown on Table 3. After 62 days there was over 95% weight loss, showing that virtually all of the polymer can be used to generate gaseous glutaraldehyde.

TABLE 3
Percent Weight Loss from Polyglutaraldehyde

| Day | Percent Loss |
|---|---|
| 1 | 3.39 |
| 2 | 3.39 |
| 3 | 3.39 |
| 4 | 3.88 |
| 5 | 2.58 |
| 6 | 2.96 |
| 7 | 3.32 |
| 8 | 4.00 |
| 9 | 4.00 |
| 10 | 4.00 |
| 13 | 4.24 |
| 14 | 4.05 |
| 15 | 3.41 |
| 16 | 3.41 |
| 17 | 3.41 |
| 18 | 2.40 |
| 19 | 1.91 |
| 20 | 1.91 |
| 21 | 1.74 |

What is claimed is:

1. A method of disinfecting a material by the slow, controlled release of a gaseous aldehyde selected from the group consisting of glyoxal, malondialdehyde, and glutaraldehyde comprising depolymerizing at a temperature from about 15° to about 40° C. without preirradiation a solid homopolymer of said aldehyde to give gaseous monomeric aldehyde in a disinfectant-effective amount and contacting said material with the gaseous aldehyde.

2. The method of claim 1 where the aldehyde is glutaraldehyde.

3. A method for the slow, controlled release of a gaseous aldehyde selected from the group consisting of glyoxal, malondialdehyde, and glutaraldehyde in a disinfectant-effective amount comprising depolymerizing at a temperature from about 15° to about 40° C. without preirradiation a solid homopolymer of said aldehyde to give a gaseous monomeric aldehyde.

4. The method of claim 3 where the aldehyde is glutaraldehyde.

5. A method of disinfecting a material by the slow, controlled release of a gaseous aldehyde selected from the group consisting of glyoxal, malondialdehyde and glutaraldehyde comprising depolymerizing at a temperature from about 15° to about 40° C. without irradiation a solid homopolymer of said aldehyde in the presence of said material to give a disinfectant-effective amount of a gaseous monomeric aldehyde.

6. The method of claim 5 where the aldehyde is glutaraldehyde.

* * * * *